US007199216B1

(12) United States Patent
Talor

(10) Patent No.: US 7,199,216 B1
(45) Date of Patent: Apr. 3, 2007

(54) PEPTIDE CONSTRUCTS FOR TREATING AUTOIMMUNE AND RELATED DISEASES

(75) Inventor: Eyal I. Talor, Baltimore, MD (US)

(73) Assignee: Cel-Sci Corporation, Vienna, VA (US)

( * ) Notice: Subject to any disclaimer, the term of this patent is extended or adjusted under 35 U.S.C. 154(b) by 624 days.

(21) Appl. No.: 10/111,602

(22) PCT Filed: Oct. 27, 2000

(86) PCT No.: PCT/US00/41647

§ 371 (c)(1),
(2), (4) Date: Apr. 26, 2002

(87) PCT Pub. No.: WO01/43695

PCT Pub. Date: Jun. 21, 2001

Related U.S. Application Data

(60) Provisional application No. 60/161,733, filed on Oct. 27, 1999.

(51) Int. Cl.
*A61K 38/00* (2006.01)
*A61K 39/00* (2006.01)
*C07K 14/00* (2006.01)
*A61K 39/385* (2006.01)

(52) U.S. Cl. ........................ 530/324; 530/402; 530/403

(58) Field of Classification Search ..................... None
See application file for complete search history.

(56) References Cited

U.S. PATENT DOCUMENTS 6,096,537 A * 8/2000 Chappel ..................... 435/325
6,100,377 A * 8/2000 Greene ....................... 530/317
6,287,565 B1 * 9/2001 Zimmerman et al. .... 424/188.1
6,358,751 B1 * 3/2002 Benichou et al. ........... 436/506

FOREIGN PATENT DOCUMENTS

WO WO 98/08416 A1 * 2/1998
WO WO 99/16710 A1 * 4/1999

OTHER PUBLICATIONS

UniProt Accession #O19507, Jan. 1, 1999, one page.*
UniProt Accession #O00664, Jul. 1, 1997, one page (same page as "U").*
Anderton, S. M. Immunology 2001, vol. 104,pp. 367-376.*

* cited by examiner

*Primary Examiner*—Christina Chan
*Assistant Examiner*—Marianne DiBrino
(74) *Attorney, Agent, or Firm*—Hahn & Voight PLLC

(57) ABSTRACT

Conjugated peptides include a first peptide component which is an antigen associated with autoimmune disease, allergy, asthma or transplantation rejection and binds to an antigen-specific receptor on a T cell, and a second peptide component which corresponds to an "antigen presenting molecule", namely, a peptide binding to a T cell surface receptor, which would normally promote T cell activation when the first peptide is bound to its antigen-specific T cell receptor. However, in this invention, the second peptide component has an amino acid sequence which is a modification of an antigen presenting T cell binding peptide, such modification blocking or inhibiting the engagement of receptor sites on the T cell surface (other than the antigen-specific T cell receptor). As a result, T cell activation is prevented, and is directed through antigen-specific T cell receptor occupation, without T cell activation, leading to antigen-specific T cell anergy and cell death. Administration of the conjugated peptide to an animal will provide protection against disease associated with the first peptide component, resulting from the elimination of the T cells bearing the antigen-specific receptors for that anti genic peptide. The conjugated peptides of this invention provide antigen-specific protection without impairing the immune response to other antigens.

1 Claim, No Drawings

PEPTIDE CONSTRUCTS FOR TREATING AUTOIMMUNE AND RELATED DISEASES

CROSS REFERENCE TO RELATED APPLICATIONS

This application claims the benefit of International application PCT/US00/41647 filed Oct. 27, 2000, and U.S. Provisional Application No. 60/161,733, filed Oct. 27, 1999.

BACKGROUND OF THE INVENTION (1) Field of Invention

The present invention relates to a conjugated peptide for conferring protection against autoimmune diseases, such as, for example, myocarditis and autoimmune thyroid disease, allergic diseases, asthma, host-versus graft and graft-versus-host disease. The present invention also relates to a method for treating or inhibiting development of autoimmune diseases, asthma, allergy, and tissue transplantation rejection and to conjugated peptides and compositions which may be used to carry out said method.

(2) Background of the Invention

A technique for modulating T cell immunological responses to a wide range of antigenic peptides has been described in the literature. This technology, referred to as LEAPS™, provides conjugated peptide immunogens (constructs) that modulate both cellular and humoral responses to treat/prevent major diseases, such as HIV infection, herpes simplex virus (HSV) infection, tuberculosis, and the like. The LEAPS constructs are conjugates of two peptides which are linked together covalently. One peptide of the conjugate is an antigen-specific epitope which will bind to the T cell receptor upon recognition. The other peptide of the conjugate is a T cell binding ligand (TCBL) derived from molecules with a known activity, such as, for example, β-2 microglobulin, IL-1, IL-2, or nonpolymorphic MHC regions, (hereinafter may be referred to as Peptide $P_2$) and which will engage other sites on the T cells to promote activation of a particular set or subset of T cells. A more detailed discussion of the LEAPS™ technology can be found in the commonly assigned U.S. Pat. No. 5,652,342, to Zimmerman, et al., the disclosure of which is incorporated herein in its entirety by reference thereto.

Briefly, the LEAPS technology allows for the preferential presentation of antigen(s) (peptide sequences) to antigen presenting cells, lymphocytes (T and B cells), dendritic cells, and other cells of the immune system. The antigen presentation is directed in such a way as to affect immune response outcome and determine with some certainty the type of immune response outcome, humoral or cellular. Thus, with the use of certain combinations of appropriate T cell binding peptide molecules together with the appropriate antigen, or the pathogenic molecule(s) of a complex antigen, forming the LEAPS construct, a cellular, antibody, or a mixed immune response can be induced by administration of the LEAPS construct.

While the LEAPS conjugates studied to date were designed to activate the T-cell immunological response to a disease causing antigen, there is also a suggestion in the aforementioned U.S. Pat. No. 5,652,342, that the LEAPS conjugated peptides can activate T suppressor cells or a subset of T suppressor cells, by selection of an appropriate TCBL which will selectively activate, for example, a subset of T suppressor cells.

SUMMARY OF THE INVENTION

It has now been discovered by the present inventor that the TCBL peptide component may be modified to prevent induction of the second signal necessary for the activation of T cells, thereby inhibiting the initiation of an immune response. Thus, the antigenic peptide component of the resulting conjugated peptide will retain its ability to interact with its receptor (antigen-specific binding site) on the T-cell, while at the same time preventing the modified TCBL peptide portion from attaching to the TCBL receptor on the same T cell surface.

By forming a new type of conjugated peptide incorporating such a modified TCBL, instead of cell activation (whether T helper cells, T suppressor cells or other T cells), with an antigenic peptide associated with an autoimmune disease or asthma or allergy, or tissue transplantation rejection, the outcome is shifted from cell activation to inhibition/suppression of the immune response in an antigen specific manner. This outcome is desired due to the fact that antigen-specific response by T cells and other cells may, in many instances, lead to an undesirable immune response outcome culminating in autoimmune disease (in the case of autoantigens), asthma and allergy (in the case of allergens) and transplantation rejection (in the case of transplantation antigens).

Thus, the present invention provides a new class of conjugated peptides comprised of two different covalently bonded peptide components, one peptide component being an antigen associated with autoimmune disease, asthma, allergy or transplantation rejection, and the second peptide component being a T cell binding ligand modified to inhibit or suppress the activation of the class or subclass of T cells to which the antigenic peptide component selectively binds, whereby the conjugated peptide will markedly decrease or completely retard undesirable immune response outcomes (e.g., autoimmune disease, asthma or allergy or transplantation rejection), while maintaining the remainder of the immune response intact.

The peptides useful as the second peptide component, $P_3$, are themselves novel molecular entities useful in the formation of the peptide constructs of this invention.

The peptide constructs of this invention may be represented by the conjugated peptide of the formula (I)

$$P_1\text{-}z\text{-}P_3 \qquad (I)$$

where $P_1$ is an antigenic peptide associated with autoimmune disease, asthma, allergy or transplantation rejection and capable of binding to antigen specific T cell receptor molecules on a class or subclass of T cells;

$P_3$ is a peptide having a sequence corresponding to the sequence of a peptide $P_2$ after modification of $P_2$ by addition, deletion or substitution of one or more amino acids or by formation of disulfide bond at one or more sites in the molecule, or a combination thereof, said peptide $P_2$ being a peptide which is able to bind to accessory molecules on the surface of said class or subclass of T cells to cause activation thereof when antigen specific T cell receptor molecules on the surface of said class or subclass of T cells bind to said antigenic peptide $P_1$, whereby attachment of peptide $P_3$ to the accessory molecule on said T cells or subset of T cells is inhibited; and, x is a direct bond or a divalent linking group.

The present invention also provides a method for treating or preventing autoimmune disease, asthma, allergy and transplantation rejection, by administering to an animal in need thereof a therapeutically effective amount of a conjugated peptide which includes two different peptide segments covalently linked to each other, directly or via a linker or spacer, wherein a first peptide segment is an antigenic peptide associated with autoimmune disease, asthma, allergy or transplantation rejection, and a second peptide segment is a T cell binding ligand modified to prevent the activation of the T cells or subset of T cells to which the first peptide segment is specifically reactive.

DETAILED DESCRIPTION OF THE INVENTION AND PREFERRED EMBODIMENTS

The amino acids in the following sequences may be set forth by the single or three letter identifying symbols as follows:

| Amino Acid | Three-letter abbreviation | One-letter symbol |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

As far as the present inventor is aware, other than a putative vaccine for Multiple Sclerosis, a disease of the central nervous system, apparently resulting from Myelin Basic Protein activation of T cells, B cells and macrophages, no effective vaccine is currently available for prevention or treatment of autoimmune disease, asthma, allergy or transplantation rejection.

In connection with the LEAPS technology as previously described in the aforementioned U.S. Pat. No. 5,652,342, it is believed that the antigen portion of these constructs interact in a direct manner, primarily to T cells, utilizing the presence of various cell surface molecules and receptors on the T cell. The antigen (in conjunction with the LEAPS molecule) interacts with the antigen-specific T cell receptor on the T cell surface, providing the primary signal—the first of two signals required for T cell activation. The LEAPS molecule, itself derived from homologous sequences of MHC (HLA) class I and Class II molecules, among others (see, e.g., U.S. Pat. No. 5,652,342) interacts with accessory molecules on the same T cell—providing the secondary signal required for T cell activation. In contrast, according to the present invention, the peptide ostensibly derived from homologous sequences of MHC (HLA) or other T cell binding ligand, is modified to such an extent that the autoimmune disease associated antigenic peptide (or asthma, allergy or transplantation rejection antigen) is still able to interact with the T cell receptor, to provide the primary signal to the T cell, while simultaneously preventing the secondary signal required for T cell activation.

Antigen specific compounds that can protect or treat autoimmune conditions such as myocarditis, or allergy, asthma and transplantation rejection are needed.

Autoimmune myocarditis is a precursor to Dilated cardiomyopathy, an end stage cardiac condition invariably requiring heart transplantation.

My-1 is the myocardiogenic peptide derived from murine cardiac myosin heavy chain (amino acids 334–352), and has been shown to induce severe myocarditis in the A/J strain of mice when injected in the presence of adjuvant (Donermeyer et al 1995, J. Exp. Med. 182:1291–1300).

The present invention was originally developed based, in part, upon the recognition that the LEAPS peptide constructs can be modified to create a new molecular entity which, rather than activating the T cells to which the antigenic peptide portion binds, will inhibit T cell activation and result instead in cell anergy, leading to cell apoptosis and cell death, of those T cells bearing that antigen specific T cell receptor (TCR). That is, the new molecular entity, referred to by the present inventor as "AdapT" construct, when applied to an autoimmune antigenic peptide (e.g., My-1 molecule) will reduce or eliminate the ability of the T cell binding ligand peptide component of the new construct to provide the "second signal" to those T cells, but without effecting the ability of the antigenic peptide component to bind to its target antigen-specific TCR. As a result, the AdapT constructs will still bind, via the antigenic peptide component, to the target T cells (via the antigen specific TCR) but without that T cell, or any of its clones, being activated. Therefore, these antigen specific T cells having TCR occupation, without T cell activation, will undergo anergy and apoptosis, leading to cell death. Since, however, the antigenic specificity is maintained, in this system, using the AdapT constructs (conjugated peptides) only the autoreactive T cells (e.g., those with the My-1 specific T cell receptor on their cell surface) are selected in this negative selection process and will thus be eliminated without harming the efficacy of the remainder of the immune response.

By applying the same technique to other autoimmune disease activating antigenic peptides or to antigenic peptides having a role in causing or initiating asthma and/or allergic reactions, or transplantation rejection, it is similarly possible to selectively cause cell death of only the cells which result in or contribute to autoimmune disease, asthma or allergy, or transplantation rejection, to undergo anergy and apoptosis, to thereby prevent, inhibit or diminish the occurrence of the autoimmune disease, asthma, allergy or transplantation rejection.

The present invention, in one specific aspect thereof, provides novel peptide constructs comprising the myosin peptide (My-1) having the formula:

```
                                          SEQ ID NO:1
Asp Ser Ala Phe Asp Val Leu Ser Phe Thr Ala Glu Glu

Lys Ala Gly Val Tyr Lys
```

attached covalently to a modified TCBL, such as, for example, a modified Peptide G ("m-G"), e.g.,

```
                                          SEQ ID NO:2
    Asn Gly Gln Glu Glu (Xaa) Ala Gly Val
```

-continued

Val Ser Thr Gly Leu Ile where Xaa is a direct bond or one or more amino acids replacing Lys;

or a modified Peptide J ("m-J"), e.g.,

SEQ ID NO:3

Asp Leu Leu Lys Asn Gly Glu Arg (Xaa) Glu Lys Val Glu where Xaa is a direct bond or one or more amino acids replacing Ile; to form conjugated peptides m-G-z-My-1 (SEQ ID NO:29) or My-1-z-M-G (SEQ ID NO:30), and m-J-z-My-1 (SEQ ID NO:31), or My-1-z-m-J (SEQ ID NO:32) where z is a direct bond or a divalent spacer or linker. Furthermore, in any of these conjugated peptides, the order of the respective amino acid sequences for SEQ ID NOs:1–3, may be reversed from the N- to C-terminals, for example, in the case of m-G-z-My-1, any of the following sequences may be formed:

NGQEEXAGVVSTGLI-z-DSAFDVLSFTAEEKAGVYK SEQ ID NO:29 or

ILGTSVVGAXEEQGN-z-DSAFDVLSFTAEEKAGVYK SEQ ID NO:33 or

NGQEEXAGVVSTGLI-z-KYVGAKEEATFSLVDFASD SEQ ID NO:34 or

ILGTSVVGAXEEQGN-z-KYVGAKEEATFSLVDFASD SEQ ID NO:35.

Similarly for any of the other conjugated peptides according to this invention the order of the amino acids in the peptide components, $P_1$ and/or $P_3$, may be arranged from the N- to C-terminal or from the C- to N-terminal.

The antigenic portion My-1 of these constructs is immunogenic in several strains of mice and in rabbits. In addition, the non-modified TCBLs G and J as well as the modified TCBLs m-G and m-J, are only poorly immunogenic, as may be judged by the lack of developing antibodies that react to these peptides (G, J, m-G or m-J).

Peptide G is from the beta-2 domain of HLA/MHC class II molecule and Peptide J is from the HLA/MHC Class I beta-2-microglobulin molecule. Other sources of TCBL's include, for example, IL-1, IL-2, IL-12, CD 28, CD40, BB-7, and the like. exemplary T cell binding ligands and specific sequences thereof. Any of these T cell binding ligands may be selected for modification according to the procedures described herein to form the new conjugated peptides of this invention which will lead to selective cell death of the T cells which bear the antigen-specific cell surface receptor for the specific autoimmune, allergen, or transplantation antigenic peptide component to which the modified TCBL is covalently bound.

In the case of autoimmune diseases, asthma, allergy, and transplantation rejection, the desired outcome is the inhibition/suppression, rather than the stimulation/activation, of the immune response, in an antigen-specific manner. This desired outcome is due to the fact that antigen-specific response by T cells and also B cells may, in many instances, lead to an undesirable immune response outcome, culminating in autoimmune disease (in the case of autoantigens), asthma or allergy (in the case of allergens) and transplantation rejection (in the case of transplantation antigens).

The ability to markedly decrease or completely retard, in an antigen specific manner, undesirable immune response outcomes, while maintaining the remainder of the immune response intact, is achieved through the conjugated peptide constructs of this invention.

The alteration of the "antigen presenting molecule" (TCBL) forming one peptide sequence component of the constructs of this invention provides for the enhancement of the antigen interaction with the antigen-specific T cell receptor. In particular, the changes (alterations) are made in those portion(s) of these antigen presenting molecule(s), which are responsible for delivering the second signal (required for T cell activation). That is, the modified TCBLs according to this invention are modified in such a way so as to lead to T cell receptor occupation (by the, e.g., autoimmune antigenic peptide, antigen associated with asthma or allergy or transplantation antigen) without T cell activation.

The occupation of the antigen-specific T cell receptor, on the T cell surface, without the availability—or with the active blockade—of a second signal to the antigen-specific T cell, leads to T cell anergy, T cell apoptosis and, eventually, cell death. Using the appropriate antigen, together with the modified antigen presenting molecule (forming the desired peptide construct) it becomes possible to preferentially remove/purge, in an antigen-specific manner, only the autoantigen, asthma, allergy or transplantation antigen reactive/causing T cell clones from humans and other animals (e.g., mammals).

The advantage of this system is that, by the administration of these constructs, antigen-specific autoreactive, asthma and allergy, and transplantation antigen reacting/causing T cell clones are removed from the host. This removal of only the disease causing cells renders the host unable to interact and respond only to disease promoting/inducing/causing antigens, while at the same time maintaining an intact immune response (necessary for maintaining the host's health) to all other antigens (including other pathogens).

This invention provides a new T cell modulation platform technology designed to synthesize novel peptide constructs that arrest/modify both cellular and humoral immune responses, and is directed towards the treatment or prevention of major diseases such as autoimmune disease, asthma, allergy and transplantation rejection.

When applied to transplantation rejection in individuals undergoing tissue, e.g., organ, transplantation, the present invention is applicable to both host-versus-graft (HvG) and graft-versus-host (GvH) rejections. In the case of HvG, the host immune response T cells are activated by donor antigens (e.g., HLA antigens and other non-HLA antigens) that are specific for the donor cells and which the host perceives as "foreign." The host immune cells attack the donor organ resulting in graft rejection. In the case of GvH, the donor cells, especially as a result of bone marrow transplantation, respond to the "foreign" host cells/organ antigens resulting in infiltration of the host's organ(s), by donor lymphocytes culminating in multiple organ failure and, often, death.

The peptide constructs of this invention may be represented by the conjugated peptide of the formula (I)

$$P_1\text{-z-}P_3 \quad \text{(I)}$$

where $P_1$ is an antigenic peptide associated with autoimmune disease, asthma, allergy or transplantation rejection and capable of binding to antigen specific T cell receptor molecules on a class or subclass of T cells;

$P_3$ is a peptide having a sequence corresponding to the sequence of a peptide $P_2$ after modification of $P_2$ by addition, deletion or substitution of one or more amino acids or by formation of disulfide bond at one or more sites in the molecule, or a combination thereof, said peptide $P_2$ being a peptide which is able to bind to accessory molecules on the surface of said class or subclass of T cells to cause activation thereof when antigen specific T cell receptor molecules on the surface of said class or subclass of T cells bind to said antigenic peptide $P_1$, whereby attachment of peptide $P_3$ to the accessory molecule on said T cells or subset of T cells is inhibited; and, z is a direct bond or a divalent linking group.

As will be appreciated from Formula (I), the peptide constructs (AdapT constructs) of this invention, include two or more peptides, which are linked together covalently. The peptide constructs may be synthesized either in vitro, e.g., by genetic engineering techniques, or by chemical peptide synthesis techniques, either as one conjoined molecule, or separately as individual molecular entities followed by covalent bonding at specific sites. One peptide of this construct, peptide $P_1$, is a specific epitope (antigen or pathogenic epitope), which will bind to the antigen-specific T cell receptor upon recognition. Representative, non-limiting examples of such peptides, suitable as $P_1$, in the present invention, include, Peptide My-1: Asp Ser Ala Phe Asp Val Leu Ser Phe Thr Ala Glu Glu Lys Ala Gly Val Tyr Lys (SEQ ID NO:1); TNF amino acid sequence 70–80: Pro Ser Thr His Leu Val Leu Ile Thr His Thr Ile (SEQ ID NO:4); Rheumatoid arthritis collagen Type II, amino acid sequence 390–402: Ile Ala Phe Lys Gly Glu Gln Gly Pro Lys Gly (SEQ ID NO:5); Multiple Sclerosis Myelin proteolipid (MPL) amino acid sequence: Lys Asn Ile Val Thr Pro Arg Thr (SEQ ID NO:6); Peptide associated with spontaneous thrombosis amino acid sequence: Gly Asp Lys Val Ser Phe Phe Cys Lys Asn Lys Glu Lys Lys Cys (SEQ ID NO:7); amino acid residues 8–15: Val Ala Asn Leu Leu Glu Asn Tyr (SEQ ID NO:8) or 125–147: Lys Ser Tyr Cys Glu Ile Ile Val Thr His Phe Pro Phe Asp Gln Gln Asn Cys Thr Met Lys Leu Gly (SEQ ID NO:9) or 195–215: Asp Thr Pro Tyr Leu Asp Ile Thr Tyr His Phe Ile Met Gln Arg Ile Pro Leu Tyr Phe Val (SEQ ID NO:10) of the acetylcholine receptor (α-subunit) associated with Myasthenia Gravis. These and other autoimmune, allergy, asthma and transplantation rejection diseases or conditions, and associated antigens, may be found in the literature, and reference is made to, for example, Clinical Laboratory Immunology, Kenneth D. McClatchey, Ed., Williams & Wilkins (USA), 1994; Clinical Immunology Principles and Practice (Volumes I and II), Robert R. Rich, Ed. in Chief, Mosby (USA), 1996; Manual of Clinical Laboratory Immunology (5th Edition), Noel R. Rose, Ed., ASM Press (USA), 1997; and Inflammation Basic Principals and Clinical Correlates (3rd Edition), John I. Gallin and Ralph Snyderman, Eds., Lippincott Williams & Wilkins (USA), 1999.

The other peptide, Peptide $P_3$, is a modified T cell binding ligand derived from molecules (TCBLs) with a known affinity to cell surface receptors present on T cells. The modified TCBL may be referred to hereinafter, for convenience, as the "AdapT molecule." Suitable sources ($P_2$) for the AdapT molecule, $P_3$, include, but are not limited to, the following; β-2 microglobulin, IL-1, IL-2, IL-7, IL-15, CD28, CD40, BB-7, and nonpolymorphic MHC regions—which, when modified, inhibit the engagement of receptor sites (other than the T cell receptor) on the T cell surface—that, would otherwise, if engaged, promote T cell activation.

Therefore, the occupation of the T cell receptor and the simultaneous blockade or inhibition of interaction of the different ligands with these secondary,—signal transducing—cell surface molecules will cause T cell anergy, cell apoptosis and lead to cell death. As these diseases (autoimmune, asthma, allergy, transplantation rejection, e.g., HvG and GvH) are caused, primarily, by the activation of antigen-specific clones of T cells (and also through B cell activation, which is dependent on T cell help), the selective removal of these clones will render the host unable to respond to these antigens. This, in turn, will result in the treatment and may lead to the cure or elimination or down regulation of these types of diseases.

Modifications of the TCBL (The AdapT Molecules)

The following are examples of types of molecular modifications to the antigen presenting molecule, TCBL, (also referred to as Peptide $P_2$) which will provide the AdapT molecule ($P_3$) which will result in the blockade or inhibition of a second signal to the antigen-specific T cell clones as described above:

1. Single or few amino acid deletion(s);

2. Single or few amino acid substitution(s) and/or addition(s);

3. Disulfide bond formation at specific site(s) in the antigen presenting molecule;

4. Combination of any and all of the changes listed in 1, 2, and 3 above;

5. An amino acid sequence (R) of at least 4 amino acids, preferably at least 6 amino acids, more preferably at least about 8 or 9 amino acids, such as from about 10 to about 50 amino acids, and wherein "R" will not bind to the antigen of interest, herein $P_1$, and will not interact with the T cell accessory molecule(s) in such a way that would cause T cell activation when the TCR is engaged by $P_1$.

The specific amino acid modifications (deletions, additions and/or substitutions) in 1, 2 and 3 above, are selected on the premise that homologous regions, in these molecules, are those most important for the overall functional integrity of these molecules. Thus, a comparison of, for example, the molecular protein structure of the HLA Class I and Class II molecular fragments derived from the intact molecules, among different species, have revealed different domains, within the structure of these molecules, that share molecular motifs. Similar observations apply to the other source molecules identified above, or any other source molecules of TCBLs.

For example, a comparison of the Human HLA Class I β-2 microglobulin molecule at positions 38 to 50 of the intact molecule, and those found in Rabbit, mouse, and guinea pig (for example), reveals homologous amino acid sequence at positions 40 to 43, 46, 49, and 50. In position 38, Mouse and Guinea Pig share the same amino acid (Glutamic acid), and in position 47, Humans and Rabbits share the same amino acid (Glutamic acid).

Based on the above, the rational place to modify these molecules is at the positions of homology in the specific sequence of this molecule. Specifically, a modification of the Class I β-2 microglobulin molecular peptide (Peptide J) (aa 38 to 50) at positions 40 to 43 ( . . . Leu-Lys-Asn-Gly . . . ) and/or at position 46 ( . . . Ile . . . ) and 47 ( . . . Glu . . . ), by substitution, addition and/or deletion of one or more amino acids, will effectively prevent or inhibit the modified peptide J from attaching to the accessory molecule on the surface of the T cells or subset of T cells containing the antigen specific T cell receptor molecules for peptide $P_1$.

Similarly, changes in position(s) of homology (i.e., conserved amino acids) in the β2 domain of the HLA Class II molecule (Peptide G) positions 135 to 149 of the intact molecule at positions 138 to 141 will result in modification of Peptide G which will prevent T cell activation when the antigenic peptide sequence ($P_1$) is bound to the antigen specific T cell receptor on the appropriate class or subclass of T cells. Preferably, the $\beta_2$ domain HLA Class II molecule, Peptide G, is modified by substitution, addition or deletion of one or more amino acids at aa 138 to 141 ( . . . Glu-Glu-Lys-Ala . . . ).

For amino acid additions and substitutions, one or more than one of the conserved amino acids will be replaced by one or more amino acids. When a conserved amino acid is replaced by more than one amino acid, the replacement amino acids (preferably no more than about 15, preferably no more than about 10, especially, no more than about 5 or 6, such as 2 or 3) may be inserted in the amino acid sequence. The amino acids substitutions may also be added as side chain attachments bonded to, or replacing, one of the conserved amino acids. While the specific sequence of the added internal or side chain replacement amino acids is not particularly critical, care should be taken to select a sequence which will not bind or interact with the sequence $P_1$ and will not interact with the T cell accessory molecule(s) on the particular set or subset of T cells bearing the antigen specific TCR for $P_1$ to inadvertently cause T cell activation when the TCR is engaged by $P_1$. For any given peptide $P_1$ the skilled practitioner will be able to determine suitable sequences for amino acid substitutions and/or additions. Usually, however, it should be sufficient to simply delete or replace one or more of the conserved (homologous) amino acids from the TCBL sequence. When replacing the conserved amino acid with a single amino acid it is generally preferred to select an amino acid having diverse properties and/or molecular size from as that of the conserved amino acid being replaced. For example, an acidic amino acid may be replaced with a basic amino acid. Other types of "non-conservative" types of amino acid substitutions are well known to the skilled practitioner.

As representative, non-limiting, examples of modifications according to 1 above, the following may be mentioned, using the TCBLs Peptide G and Peptide J as specific embodiments of peptide $P_2$.

Type 1-(a) Single Amino Acid (aa) Deletion

For Peptide G:
(1) delete Glu (aa138);
(2) delete Glu (aa139);
(3) delete Lys (aa140);
(4) delete Ala (aa141).

For Peptide J:
(1) delete Leu (aa40);
(2) delete Lys (aa41);
(3) delete Asn (aa42);
(4) delete Gly (aa43);
(5) delete Ile (aa46);
(6) delete Glu (aa47).

Type 1-(b) Few Amino Acid Deletions

For Peptide G:
(1) delete Glu-Glu (aa138–139)
(2) delete Glu-Lys (aa139–140)
(3) delete Glu (aa138) and Lys (aa140)
(4) delete Glu (aa138) and Ala (aa141)
(5) delete Glu (aa139), Lys (aa140) and Ala (aa142).

For Peptide J:
(1) delete Leu (aa40) and Lys (aa41);
(2) delete Leu (aa40) and Ile (aa46);
(3) delete Lys (aa41) and Asn (aa42);
(4) delete Ile (aa46) and Glu (aa47).

Type 2-(a) Single Amino Acid Substitution or Insertion

For Peptide G:
(1) replace Glu (aa138) with Ala or Ile or Leu or Val or Gly or Phe or Tyr or Thr or Ser or Lys or Arg or His or Asn or Gln;
(2) insert Ile or Leu or Val or Gly or Ala or Phe or Tyr or Thr or Ser or Lys or Arg or His or Asn or Gln after Glu (aa139);
(3) insert Glu or Asp or Ser, etc., after Lys (aa140);
(4) insert Gly or Tyr or Lys, etc., after Ala (aa141);
(5) replace Lys (aa140) with Gly or Val or Pro or Thr or Tyr or Asp or Asn, etc.

For Peptide J:
(1) insert Asn after Leu (aa40);
(2) insert Leu after Gly (aa41);
(3) insert Ile after Asn (aa42);
(4) insert Glu after Gly (aa43);
(5) insert Gly after Ile (aa46);
(6) insert Asn after Glu (aa47).
(7) replace Gly (aa41) with Pro or Ser or Thr or Phe or Tyr or Trp or Lys or Arg or His or Asp or Glu or Asn or Gln.

Type 2-(b) Multiple (Few) Amino Acid Substitutions/Insertions

For Peptide G:
(1) insert Ala-Lys after or for Glu (aa138);
(2) insert Glu-Lys after Lys (aal40);
(3) insert Asp-Glu-Arg after or for Lys (aa140);
(4) insert Gly-Ala after or for Lys (aa140);
(5) insert Glu after Glu (aa138) and insert Lys after Ala (aa140;
(6) insert Gly after Glu (aa139) and insert Lys after Lys (aa140);
(7) insert Ile, Glu and Gly after Glu (aa139), Lys (aa140) and Ala (aa141), respectively;
(8) replace Glu (aa139) with Tyr and insert Ser-Ala after Lys (aa140).

For Peptide J:
(1) insert Ile after Leu (aa40) and insert Gly after Lys (aa41);
(2) insert Asn after Lys (aa41) and insert Glu after Asn (aa42);
(3) insert Leu and Gly after aa42 and 43, respectively;
(4) insert Ile and Glu after aa 43 and 46, respectively;
(5) insert Lys and Leu after aa46 and aa47, respectively;
(6) insert Glu and Leu after aa 40 and 46, respectively;
(7) replace Leu (aa40) with Lys or Tyr and replace Ile (aa46) with Ala or Thr;
(8) replace Asn (aa41) with Asp-Ala;
(9) replace Ile (aa46) with Glu and insert Ala after Gly (aa43).

Type 3-(a) Disulfide Bond Formation

For Peptide G:
(1) insert sulfhydryl groups, e.g., Met or Cys, between Asn (aa135) and Gly (aa136) and between Lys (aa140) and Ala (aa141) and form a disulfide bond;
(2) insert Cys or Met between Gly (aa136) and Gln (aa137) and between Ala (aa141) and Gly (aa142) and form a disulfide bond;

(3) insert Cys or Met between Asn (aa135) and Gly (aa136) and between Gly (aa142) and Val (aa143) and form a disulfide bond;

For Peptide J:

(1) insert sulfhydryl groups, e.g., Cys or Met between Asn (aa42) and Gly (aa43) and between Asp (aa38) and Leu (aa39) and form a disulfide bond;

(2) insert Cys or Met between Asp (aa38) and Leu (aa39) and between Gly (aa43) and Glu (aa44) and form a disulfide bond;

(3) insert Cys or Met between Glu (aa44) and Arg (aa45) and between Leu (aa39) and Leu (aa40) and form a disulfide bond;

(4) insert Met or Cys between Arg (aa45) and Ile (aa46) and between Asp (aa38) and Leu (aa39) and form a disulfide bond.

The modification in type 5 above is actually a specific example of amino acid addition/substitution according to type 2 above where "R" represents an amino acid sequence of at least 4 amino acids, preferably at least 6 amino acids, more preferably at least about 8 or 9 amino acids, such as from about 8 to about 50 amino acids, more preferably from about 10 to about 20 amino acids, and wherein "R" will not bind to the antigen of interest, herein $P_1$, and will not interact with the T cell accessory molecule(s) in such a way that would cause T cell activation when the TCR is engaged by $P_1$.

The "R" modifying group may be linked to the free terminal end of the non-modified TCBL peptide, $P_2$, or R may be linked to an already modified TCBL wherein the modification is at a different site than that to which R is to be linked. R may also be linked to an internal amino acid of $P_2$ (preferably, one of the "conserved" amino acids) or R may be linked to an amino acid substitution for a conserved amino acid, or R may be inserted between two internal amino acids of $P_2$, usually and preferably, at a position located at least about 2, preferably at least about 4 amino acids from either the N- or C-terminal of $P_2$.

Examples of modifying groups R, include, for example, a portion of beta-pleated sheet of MHC Class I, and a portion of the alpha-helical structure of MHC Class I, (see "Fundamental Immunology" W. E. Paul, Raven Press (USA) 1986).

As an example of the beta-pleated sheet modifying group R, mention may be made of, for example, the amino acid sequence at positions (residues) 95–118:

```
                                              SEQ ID NO:12
Leu Gln Ser Met Tyr Gly Cys Asp Val Gly

Pro Asp Gly Arg Leu Leu Arg Gly His Asp

Gln Tyr Ala Ile
```

The entirety of the sequence SEQ ID NO:12 or a portion thereof, usually of at least about 8, preferably, at least about 10 consecutive amino acids, such as, for example, positions 99–113:

```
                                              SEQ ID NO:13
Tyr Gly Cys Asp Val Gly Pro Asp Gly Arg

Leu Leu Arg Gly His
```

positions 96–111:

```
                                              SEQ ID NO:14
Gln Ser Met Tyr Gly Cys Asp Val Gly Pro

Asp Gly Arg Leu Leu Arg
```

or positions 100–118:

```
                                              SEQ ID NO:15
Gly Cys Asp Val Gly Pro Asp Gly Arg Leu

Leu Arg Gly His Asp Gln Tyr Ala Ile
```

or positions 100–115:

```
                                              SEQ ID NO:36
Gly Cys Asp Val Gly Pro Asp Gly Arg Leu

Leu Arg Gly His Asp Gln
```

may be attached to the TCBL, $P_2$, at a terminal thereof (the end not bonded to $P_1$) directly or via linker or spacer x or the R modifying group may be linked to or replace an internal amino acid or inserted between two adjacent internal amino acids of $P_2$ (thus forming a branch or side chain group), preferably one of the homologous (conserved) amino acids as described above, and preferably spaced by at least 2, preferably at least 4, amino acids from the N- or C-terminal of $P_2$.

As an example of a portion of the alpha-helical structure of MHC Class I, mention may be made of, for example, the amino acid sequence at residues 64–87:

```
                                              SEQ ID NO:16
Thr Gln Ile Tyr Lys Ala His Ala Gln Thr

Asp Arg Glu Ser Leu Arg Asn Leu Arg Gly

Tyr Tyr Asn Gln
```

or a portion thereof, usually at least about 8 amino acids, such as, for example, residues 64–79 having the sequence

```
                                              SEQ ID NO:17
Thr Gln Ile Tyr Lys Ala His Ala Gln Thr

Asp Arg Glu Ser Leu Arg
```

or residues 79–87 having the sequence

```
                                              SEQ ID NO:18
Arg Asn Leu Arg Gly Tyr Tyr Asn Gln
```

These R groups may, similarly, be linked to the unoccupied (free) terminal of $P_2$. Alternatively, to form a side or branched chain on $P_2$, the R group may be linked to an internal amino acid or substituted internal amino acid in $P_2$. When the R group replaces an internal amino acid, it preferably replaces a conserved amino acid in the TCBL sequence, $P_2$, or still further, one of the amino acids of the R group, preferably the N- or C-terminal amino acid of R, may be inserted between two adjacent amino acids in $P_2$. The side chain R group will preferably be spaced by at least 2, preferably at least 4 amino acids from the N- or C-terminal amino acid of $P_2$. Representative examples of R group modifications to form the AdapT molecule $P_3$ include, for example, in the case of Peptide G, insertion of R between amino acid residues at positions 135 and 136, between positions 136 and 137, between positions 137 and 138, between positions 138 and 139 and/or between positions 139 and 140; or addition of the R group to Asn at aa position 135 or to Ile at position 149 or to an internal amino acid, such as to Glu at aa138 or aa139. Still further, the R group may be inserted in place of an internal amino acid, such as at positions 138, 139, 140 or 141.

The peptide construct according to modification 5 above, may be represented by the following formula (II):

$$P_1\text{-z-}(P_2\text{-R}) \qquad \text{(II)}$$

where $P_1$, $P_2$, R and z are as previously defined, and ($P_2$-R=$P_3$) and where R may be linked to the free terminal amino acid of $P_2$ or R may substitute for or be linked to an internal amino acid of $P_2$. Thus, $P_2$-R may take the form (A1) $a_1$-$a_2$- . . . $a_n$-R (where $a_1$, $a_2$, $a_n$ represent the first, second and nth amino acids in the amino acid sequence of $P_2$, and where $a_1$ represents the terminal amino acid linked to $P_1$ directly or via z, and $a_n$ represents the free or unoccupied terminal amino acid) or $P_2$R may take the form (A2) $a_1$- . . . $a_m$(R) . . . $a_n$, where $a_1$ and $a_n$ have the same meanings as above and $a_m$ represents an internal amino acid of $P_2$ or a substituted amino acid for the mth amino acid in the sequence of $P_2$ or an amino acid of R.

For example, in the case of Peptide G, having the amino acid sequence (single letter format): NGQEEKAGVVSTGLI (SEQ ID NO:11) and R being taken from amino acid (aa) positions 95–118 ($A_{95-118}$) (SEQ ID NO:12) or aa positions 99–113 ($A_{99-113}$) (SEQ ID NO:13) or aa positions 96–111 ($A_{96-111}$) (SEQ ID NO:14) or aa positions 100–118 ($A_{100-118}$) (SEQ ID NO:15) of the beta-pleated sheet of MHC Class I representative AdapT molecules ($P_3$) according to the invention include the following:

```
                                                SEQ ID NO:19
ILGTSVVGADEEQGN-z1-LQSMYGCDVGPDGRLLRGHDGYAI (III)
 Peptide G     linker    A95–118
```

or

```
                                                SEQ ID NO:20
NGQEEDAGVVSTGLI-z1-LQSMYGCDVGPDGRLLRGHDGYAI (III-1)
  Peptide G    linker   A95–118
```

or

```
                                                SEQ ID NO:21
NGQEEDAGVVSTGLI-z1-IAYGDHGRLLRGDPGVDCGYMSQL (III-2)
  Peptide G     linker    A95–118
```

or

```
                                                SEQ ID NO:22
ILGTSVVGADEEQGN-z1-IAYGDHGRLLRGDPGVDCGYMSQL (III-3)
  Peptide G    linker     A95–118
```

where $z_1$ represents a divalent spacer, such as, for example, GGG, GGGGS, and the like; or

```
                              (IV) SEQ ID NO: 23
NGQEEDAGVVSTGLI
     |
     A100-115
```

-continued

```
                              (V) SEQ ID NO: 24
NGQEEDAGVVSTGLI
    | |
    | A99-113
    A95-118

                              (VI) SEQ ID NO: 25
NGQEELKAGVVSTGLI
     |
     A96-118
```

In formula (VI), the first leucine (L) corresponds to the amino acid residue 95 of SEQ ID NO:12 inserted between the Glu (E) and Lys (K) amino acid residues of Peptide G.

In the above formulas for representative AdapT molecules $P_3$, the peptide of formula (III) will preferably be linked to $P_1$ (directly or via divalent linker or spacer z) via the free terminal {Ile (I) or Asn (N)} amino acid. The AdapT molecules represented by formulas (IV), (V) and (VI) may be linked to $P_1$ at either the Asn (N) or the Ile (I) terminal amino acids. In this regard, it should be understood that the order of the C- and N-terminals of any of these peptide sequences can be reversed Thus, conjugated peptides effective for treating myocarditis, for example, can have any of the following representative formulas incorporating My-1 (SEQ ID NO:1):

```
                                                  SEQ ID NO: 26
A96-118-GGGGS-NGQEEKAGVVSTGLI-GGG-KYVGAKEEATFSLVFASD
                                                  SEQ ID NO: 27
NGQEEDAGVVSTGLI-GGG-DSAFDVLSFTAEEKAGVYK
     |
     A99-113
                                                  SEQ ID NO: 28
NGQEEDAGVVSTGLI-GGG-DSAFDVLSFTAEEKAGVYK
    | |
    | A99-113
    A100-118
```

In each case, however, the side chain beta-pleated amino acid sequence will not interfere with the attachment of $P_1$ to its TCR but will prevent, or at least greatly inhibit, attachment of the modified TCBL (AdapT molecule) to the T cell accessory molecules on the surface of that T cell and its clones, thereby preventing (or at least substantially diminishing) T cell activation in an antigen-specific manner.

The peptide constructs according to this invention as well as the individual components $P_1$ and $P_3$, (including $P_2$ and R) may be formed by any of the known techniques for forming peptides, including, for example, solid phase peptide synthesis, such as described, for example, by Merrifield, R. B., 1963, J. of Am. Chem. Soc., 85:2149–2154. It is also within the scope of the invention to produce the individual peptides and/or peptide conjugates by genetic engineering based on the corresponding gene sequences. Reference may also be had, for example, to the aforementioned U.S. Pat. No. 5,652,342, for further details as to synthesis methods.

There is also no particular restriction on the size of the individual peptides $P_1$ or $P_3$, provided however, that the minimum length will usually be at least 4, and preferably at least 6, such as about 8 or 9 amino acids, usually no more than about 20 amino acids, for peptide $P_1$, which will allow binding to the antigen specific binding site, and similarly, for peptide $P_3$ to effectively block/inhibit binding to the accessory molecule.

Where the individual peptide components or the peptide construct are longer than about 40 amino acids, especially longer than about 50 amino acids, it will often be necessary and preferred, in the case of solid phase peptide synthesis, to synthesize individual consecutive lengths of no more than about 40 amino acids, preferably no more than about 30 amino acids, and then covalently link the consecutive sections by techniques well known in the art, such as, for example, the aforementioned U.S. Pat. No. 5,652,342.

There is also no particular restriction on the total length of the peptide constructs of this invention but, they will usually be at least about 20 amino acids in length, preferably at least about 25 to 30 amino acids in length and usually no longer than about 300 amino acids, preferably up to about 200 or more amino acids, especially preferably, from about 20 to about 200 amino acids, more preferably from about 20 to about 100 amino acids, such as, for example, from about 30 to 80 amino acids, more preferably form about 30 to 60 amino acids.

The peptide constructs of this invention may be used as therapeutic compounds for the treatment of autoimmune diseases and conditions, and for treatment of allergy and asthma and transplantation rejection in humans and other animals, preferably mammals, including household pets, such as dogs and cats, as well as livestock, such as bovine, porcine and equine. The peptide constructs may also be used prophylactically in humans and other animals to inhibit the likelihood of onset of autoimmune disease, allergy or asthma in individuals considered to be at risk for such conditions, whether as a result of genetic factors or environmental exposure, age or other factors.

The peptide conjugates may be administered alone (in a suitable vehicle depending on the mode of administration) or in combination or in conjunction with an adjuvant or other active component, including, for example, any conventional treatment therapy for the particular condition to be treated.

Preparations containing the subject peptide constructs may be administered by any of the known methods for peptide administration, including, for example, intramuscularly (IM), subcutaneously (SC), transdermally, or intranasally or orally, or as an inhalant preparation or intravenously. These preparations may be formulated as unit dosages to provide a therapeutically effective amount of the conjugated peptide, preferably an amount in the range of 10 to 100 micrograms per kilogram of body weight. Usually, the therapeutic or prophylactic preparations will be administered over a prolonged course of administration, such as weekly, bi-weekly, monthly, quarterly, semi-annually or annually, often for a patient's lifetime. The prolonged treatment will generally be necessary since newly formed or mature T cells with the antigen-specific TCR of interest, can be expected to be produced by the bone marrow and re-enter into the blood and lymphatic system, even after the initial treatment, over the course of an individual's lifetime.

The peptide constructs of this invention are also useful in connection with prevention or inhibition of transplantation rejection in animals (humans and other mammals) undergoing tissue or organ transplantation. Such transplantation rejection may take the form of host-versus-graft (HvG) rejection or as graft-versus-host (GvH) rejection, the latter being especially severe in immunocompromised and severely immunosuppressed individuals.

In the case of HvG, the host immune response cells, T cells, B cells, and macrophages, are activated by donor antigens (e.g., HLA antigens and other non-HLA antigens) that are specific for the donor cells and which the host perceives as "foreign." The host immune cells attack the donor organ resulting in graft rejection.

In the case of GvH, the donor cells (especially as a result of bone marrow transplantation) respond to the host's cells/organs(s) as foreign antigens resulting in cellular infiltration of the host's organs, culminating in multiple organ failure, and often, death.

The use of the peptide constructs of this invention, for treatment of GvH, wherein $P_1$ is a transplantation antigen, e.g., a sequence derived from the host antigens (e.g., HLA class II, HLA class I and other host specific antigens) may be mixed with donor bone marrow cells prior to infusion. The resulting cell preparation is then administered, such as by intravenous infusion, to the recipient. The mixture of donor specific peptide construct(s) may be infused separately into the recipient following bone marrow engagement (transplantation) every other day for 2 to 3 weeks. This treatment will cause only those bone marrow donor cells that may be sensitized to the host cell antigens to undergo anergy, apoptosis and cell death, thereby inhibiting or diminishing GvH disease.

For treating transplantation rejection in the case of organ donation, i.e., HvG, the host may be injected with from about 10 to about 100 micrograms per kilogram of body weight with peptide construct(s) using as $P_1$ unique antigen(s) of the donor specific organ antigen, or preferably, a mixture of different donor specific antigens $P_1$. In this case, the different $P_1$'s may be linked to the same or different AdapT molecules, $P_3$, for example, as $P_{1a}$-z-$P_3$+$P_{1a}$-z-$P_3$, etc., or as $P_{1a}$-$z_1$-$P_{1b}$-$z_2$-$P_3$ or $P_{1a}$-$z_1$-$P_3$-$z_2$-$P_{1b}$, etc. Dosage amounts and modes of administration are similar to the dosages and modes of administration for GvH, namely, for example, about 10 to 100 micrograms/kilogram body weight, via intravenous infusion, every other day for 2 to 3 weeks, and then monthly, bi-monthly, semi-annually or annually, thereafter, in the recipient following organ transplantation. This treatment will result in depletion of the recipient's immune T cells which would otherwise be available to react with donor organ antigens, leading to the inhibition of host-vs-graft rejection.

What is claimed is:

1. A conjugated peptide consisting of the formula

DSAFDVLSFTAEEKAGVYK-z-NGQEEXAGVVSTGLI SEQ ID NO:30 or

NGQEEXAGVVSTGLI-z-DSAFDVLSFTAEEKAGVYK SEQ ID NO:29 wherein z is a direct bond or a divalent linker and X represents an amino acid other than Lys.

* * * * *

UNITED STATES PATENT AND TRADEMARK OFFICE

CERTIFICATE OF CORRECTION

PATENT NO. : 7,199,216 B1
APPLICATION NO. : 10/111602
DATED : April 3, 2007
INVENTOR(S) : Talor It is certified that error appears in the above-identified patent and that said Letters Patent is hereby corrected as shown below:

On the Title Page, Item (56) replace “WO 98/08416” with --WO 98/06416--.

Signed and Sealed this

Twenty-second Day of May, 2007

JON W. DUDAS
*Director of the United States Patent and Trademark Office*

SEQUENCE LISTING

```
<160> NUMBER OF SEQ ID NOS: 36

<210> SEQ ID NO 1
<211> LENGTH: 19
<212> TYPE: PRT
<213> ORGANISM: artificial sequence
<220> FEATURE:
```

-continued

```
<223> OTHER INFORMATION: peptide construct comprising myosin peptide
      (My-1)

<400> SEQUENCE: 1

Asp Ser Ala Phe Asp Val Leu Ser Phe Thr Ala Glu Glu Lys Ala Gly
1               5                   10                  15

Val Tyr Lys


<210> SEQ ID NO 2
<211> LENGTH: 18
<212> TYPE: PRT
<213> ORGANISM: artificial sequence
<220> FEATURE:
<223> OTHER INFORMATION: peptide construct comprising myosin peptide
      (My-1)
<220> FEATURE:
<221> NAME/KEY: MISC_FEATURE
<222> LOCATION: (6)..(6)
<223> OTHER INFORMATION: Xaa is a single amino acid or is not present
<220> FEATURE:
<221> NAME/KEY: MISC_FEATURE
<222> LOCATION: (9)..(9)
<223> OTHER INFORMATION: Xaa is a single amino acid or is not present
<220> FEATURE:
<221> NAME/KEY: MISC_FEATURE
<222> LOCATION: (7)..(7)
<223> OTHER INFORMATION: Xaa is a single amino acid or is not present
<220> FEATURE:
<221> NAME/KEY: MISC_FEATURE
<222> LOCATION: (8)..(8)
<223> OTHER INFORMATION: Xaa is a single amino acid or is not present
<220> FEATURE:
<221> NAME/KEY: MISC_FEATURE
<222> LOCATION: (6)..(9)
<223> OTHER INFORMATION: if any x is not present it is understood that
      subsequent positions will be shifted without any change to recited
      features

<400> SEQUENCE: 2

Asn Gly Gln Glu Glu Xaa Xaa Xaa Xaa Ala Gly Val Val Ser Thr Gly
1               5                   10                  15

Leu Ile


<210> SEQ ID NO 3
<211> LENGTH: 16
<212> TYPE: PRT
<213> ORGANISM: artificial sequence
<220> FEATURE:
<223> OTHER INFORMATION: peptide construct comprising myosin peptide
      (My-1 3)
<220> FEATURE:
<221> NAME/KEY: MISC_FEATURE
<222> LOCATION: (9)..(9)
<223> OTHER INFORMATION: Xaa is a single amino acid other than Ile or is
      not present
<220> FEATURE:
<221> NAME/KEY: MISC_FEATURE
<222> LOCATION: (9)..(12)
<223> OTHER INFORMATION: if any x is not present it is understood that
      subsequent positions will be shifted without any change to recited
      features
<220> FEATURE:
<221> NAME/KEY: MISC_FEATURE
<222> LOCATION: (10)..(10)
<223> OTHER INFORMATION: Xaa is a single amino acid other than Ile or is
      not present
<220> FEATURE:
<221> NAME/KEY: MISC_FEATURE
<222> LOCATION: (12)..(12)
<223> OTHER INFORMATION: Xaa is a single amino acid other than Ile or is
      not present
<220> FEATURE:
<221> NAME/KEY: MISC_FEATURE
```

-continued

```
<222> LOCATION: (11)..(11)
<223> OTHER INFORMATION: Xaa is a single amino acid other than Ile or is
      not present

<400> SEQUENCE: 3

Asp Leu Leu Lys Asn Gly Glu Arg Xaa Xaa Xaa Xaa Glu Lys Val Glu
1               5                   10                  15


<210> SEQ ID NO 4
<211> LENGTH: 12
<212> TYPE: PRT
<213> ORGANISM: artificial sequence
<220> FEATURE:
<223> OTHER INFORMATION: peptide construct comprising tumor necrosis
      factor TNF

<400> SEQUENCE: 4

Pro Ser Thr His Leu Val Leu Ile Thr His Thr Ile
1               5                   10


<210> SEQ ID NO 5
<211> LENGTH: 11
<212> TYPE: PRT
<213> ORGANISM: artificial sequence
<220> FEATURE:
<223> OTHER INFORMATION: peptide construct of rheumatoid arthritis
      collagen type II

<400> SEQUENCE: 5

Ile Ala Phe Lys Gly Glu Glu Gly Pro Lys Gly
1               5                   10


<210> SEQ ID NO 6
<211> LENGTH: 8
<212> TYPE: PRT
<213> ORGANISM: artificial sequence
<220> FEATURE:
<223> OTHER INFORMATION: peptide construct comprising multiple sclerosis
      myelin proteolipid

<400> SEQUENCE: 6

Lys Asn Ile Val Thr Pro Arg Thr
1               5


<210> SEQ ID NO 7
<211> LENGTH: 15
<212> TYPE: PRT
<213> ORGANISM: artificial sequence
<220> FEATURE:
<223> OTHER INFORMATION: peptide construct comprising acetylcholine
      receptor, alpha-subunit associated with Myasthenia Gravis

<400> SEQUENCE: 7

Gly Asp Lys Val Ser Phe Phe Cys Lys Asn Lys Glu Lys Lys Cys
1               5                   10                  15


<210> SEQ ID NO 8
<211> LENGTH: 8
<212> TYPE: PRT
<213> ORGANISM: artificial sequence
<220> FEATURE:
<223> OTHER INFORMATION: peptide construct comprising acetylcholine
      receptor, alpha-subunit associated with Myasthenia Gravis 2

<400> SEQUENCE: 8

Val Ala Asn Leu Leu Glu Asn Tyr
1               5
```

-continued

```
<210> SEQ ID NO 9
<211> LENGTH: 23
<212> TYPE: PRT
<213> ORGANISM: artificial sequence
<220> FEATURE:
<223> OTHER INFORMATION: peptide construct comprising acetylcholine
      receptor, alpha-subunit associated with Myasthenia Gravis 3

<400> SEQUENCE: 9

Lys Ser Tyr Cys Glu Ile Ile Val Thr His Phe Pro Phe Asp Gln Gln
1               5                   10                  15

Asn Cys Thr Met Lys Leu Gly
            20


<210> SEQ ID NO 10
<211> LENGTH: 21
<212> TYPE: PRT
<213> ORGANISM: artificial sequence
<220> FEATURE:
<223> OTHER INFORMATION: peptide construct comprising acetylcholine
      receptor, alpha-subunit associated with Myasthenia Gravis 4

<400> SEQUENCE: 10

Asp Thr Pro Tyr Leu Asp Ile Thr Tyr His Phe Ile Met Gln Arg Ile
1               5                   10                  15

Pro Leu Tyr Phe Val
            20


<210> SEQ ID NO 11
<211> LENGTH: 15
<212> TYPE: PRT
<213> ORGANISM: artificial sequence
<220> FEATURE:
<223> OTHER INFORMATION: peptide G

<400> SEQUENCE: 11

Asn Gly Gln Glu Glu Lys Ala Gly Val Val Ser Thr Gly Leu Ile
1               5                   10                  15


<210> SEQ ID NO 12
<211> LENGTH: 24
<212> TYPE: PRT
<213> ORGANISM: artificial sequence
<220> FEATURE:
<223> OTHER INFORMATION: peptide construct comprising beta-pleated sheet
      of MHC Class I

<400> SEQUENCE: 12

Leu Gln Ser Met Tyr Gly Cys Asp Val Gly Pro Asp Gly Arg Leu Leu
1               5                   10                  15

Arg Gly His Asp Gln Tyr Ala Ile
            20


<210> SEQ ID NO 13
<211> LENGTH: 15
<212> TYPE: PRT
<213> ORGANISM: artificial sequence
<220> FEATURE:
<223> OTHER INFORMATION: peptide construct comprising beta-pleated sheet
      of MHC Class I (2)

<400> SEQUENCE: 13

Tyr Gly Cys Asp Val Gly Pro Asp Gly Arg Leu Leu Arg Gly His
1               5                   10                  15
```

-continued

<210> SEQ ID NO 14
<211> LENGTH: 16
<212> TYPE: PRT
<213> ORGANISM: artificial sequence
<220> FEATURE:
<223> OTHER INFORMATION: peptide construct comprising beta-pleated sheet of MHC Class I (3)

<400> SEQUENCE: 14

Gln Ser Met Tyr Gly Cys Asp Val Gly Pro Asp Gly Arg Leu Leu Arg
1 5 10 15

<210> SEQ ID NO 15
<211> LENGTH: 19
<212> TYPE: PRT
<213> ORGANISM: artificial sequence
<220> FEATURE:
<223> OTHER INFORMATION: peptide construct comprising beta-pleated sheet of MHC Class I (4)

<400> SEQUENCE: 15

Gly Cys Asp Val Gly Pro Asp Gly Arg Leu Leu Arg Gly His Asp Gln
1 5 10 15

Tyr Ala Ile

<210> SEQ ID NO 16
<211> LENGTH: 24
<212> TYPE: PRT
<213> ORGANISM: artificial sequence
<220> FEATURE:
<223> OTHER INFORMATION: peptide construct comprising alpha-helical structure of MHC Class I

<400> SEQUENCE: 16

Thr Gln Ile Tyr Lys Ala His Ala Gln Thr Asp Arg Glu Ser Leu Arg
1 5 10 15

Asn Leu Arg Gly Tyr Tyr Asn Gln
20

<210> SEQ ID NO 17
<211> LENGTH: 16
<212> TYPE: PRT
<213> ORGANISM: artificial sequence
<220> FEATURE:
<223> OTHER INFORMATION: peptide construct comprising alpha-helical structure of MHC Class I (2)

<400> SEQUENCE: 17

Thr Gln Ile Tyr Lys Ala His Ala Gln Thr Asp Arg Glu Ser Leu Arg
1 5 10 15

<210> SEQ ID NO 18
<211> LENGTH: 9
<212> TYPE: PRT
<213> ORGANISM: artificial sequence
<220> FEATURE:
<223> OTHER INFORMATION: peptide construct comprising alpha-helical structure of MHC Class I (3)

<400> SEQUENCE: 18

Arg Asn Leu Arg Gly Tyr Tyr Asn Gln
1 5

<210> SEQ ID NO 19
<211> LENGTH: 39
<212> TYPE: PRT
<213> ORGANISM: artificial sequence -continued
<220> FEATURE:
<223> OTHER INFORMATION: peptide construct
<220> FEATURE:
<221> NAME/KEY: MISC_FEATURE
<222> LOCATION: (15)..(16)
<223> OTHER INFORMATION: A divalent bond between 15 and 16

<400> SEQUENCE: 19

Ile Leu Gly Thr Ser Val Val Gly Ala Asp Glu Glu Gln Gly Asn Leu
1               5                   10                  15

Gln Ser Met Tyr Gly Cys Asp Val Gly Pro Asp Gly Arg Leu Leu Arg
            20                  25                  30

Gly His Asp Gly Tyr Ala Ile
        35

<210> SEQ ID NO 20
<211> LENGTH: 39
<212> TYPE: PRT
<213> ORGANISM: artificial sequence
<220> FEATURE:
<223> OTHER INFORMATION: peptide construct
<220> FEATURE:
<221> NAME/KEY: MISC_FEATURE
<222> LOCATION: (15)..(16)
<223> OTHER INFORMATION: A divalent bond between 15 and 16

<400> SEQUENCE: 20

Asn Gly Gln Glu Glu Asp Ala Gly Val Val Ser Thr Gly Leu Ile Leu
1               5                   10                  15

Gln Ser Met Tyr Gly Cys Asp Val Gly Pro Asp Gly Arg Leu Leu Arg
            20                  25                  30

Gly His Asp Gly Tyr Ala Ile
        35

<210> SEQ ID NO 21
<211> LENGTH: 39
<212> TYPE: PRT
<213> ORGANISM: artificial sequence
<220> FEATURE:
<223> OTHER INFORMATION: peptide construct
<220> FEATURE:
<221> NAME/KEY: MISC_FEATURE
<222> LOCATION: (15)..(16)
<223> OTHER INFORMATION: A divalent bond between 15 and 16

<400> SEQUENCE: 21

Asn Gly Gln Glu Glu Asp Ala Gly Val Val Ser Thr Gly Leu Ile Ile
1               5                   10                  15

Ala Tyr Gly Asp His Gly Arg Leu Leu Arg Gly Asp Pro Gly Val Asp
            20                  25                  30

Cys Gly Tyr Met Ser Gln Leu
        35

<210> SEQ ID NO 22
<211> LENGTH: 39
<212> TYPE: PRT
<213> ORGANISM: artificial sequence
<220> FEATURE:
<223> OTHER INFORMATION: peptide construct
<220> FEATURE:
<221> NAME/KEY: MISC_FEATURE
<222> LOCATION: (15)..(16)
<223> OTHER INFORMATION: A divalent bond between 15 and 16

<400> SEQUENCE: 22

Ile Leu Gly Thr Ser Val Val Gly Ala Asp Glu Glu Gln Gly Asn Ile

-continued

```
1               5                   10                  15

Ala Tyr Gly Asp His Gly Arg Leu Leu Arg Gly Asp Pro Gly Val Asp
            20                  25                  30

Cys Gly Tyr Met Ser Gln Leu
        35


<210> SEQ ID NO 23
<211> LENGTH: 15
<212> TYPE: PRT
<213> ORGANISM: artificial sequence
<220> FEATURE:
<223> OTHER INFORMATION: peptide construct
<220> FEATURE:
<221> NAME/KEY: PEPTIDE
<222> LOCATION: (6)..(6)
<223> OTHER INFORMATION: an amino acid from positions 100-115 of SEQ ID
      NO. 15 of beta-pleated sheet of MHC Class I

<400> SEQUENCE: 23

Asn Gly Gln Glu Glu Asp Ala Gly Val Val Ser Thr Gly Leu Ile
1               5                   10                  15


<210> SEQ ID NO 24
<211> LENGTH: 15
<212> TYPE: PRT
<213> ORGANISM: artificial sequence
<220> FEATURE:
<223> OTHER INFORMATION: peptide construct
<220> FEATURE:
<221> NAME/KEY: PEPTIDE
<222> LOCATION: (5)..(5)
<223> OTHER INFORMATION: an amino acid from positions 95-118 of SEQ ID
      NO. 12 of beta-pleated sheet of MHC Class I
<220> FEATURE:
<221> NAME/KEY: PEPTIDE
<222> LOCATION: (7)..(7)
<223> OTHER INFORMATION: an amino acid from positions 99-113 of SEQ ID
      NO. 13 of beta-pleated sheet of MHC Class I

<400> SEQUENCE: 24

Asn Gly Gln Glu Glu Asp Ala Gly Val Val Ser Thr Gly Leu Ile
1               5                   10                  15


<210> SEQ ID NO 25
<211> LENGTH: 16
<212> TYPE: PRT
<213> ORGANISM: artificial sequence
<220> FEATURE:
<223> OTHER INFORMATION: peptide construct
<220> FEATURE:
<221> NAME/KEY: PEPTIDE
<222> LOCATION: (6)..(6)
<223> OTHER INFORMATION: an amino acid from positions 96-118 of
      shortened SEQ ID NO. 12 of beta-pleated sheet of MHC Class I

<400> SEQUENCE: 25

Asn Gly Gln Glu Glu Leu Lys Ala Gly Val Val Ser Thr Gly Leu Ile
1               5                   10                  15


<210> SEQ ID NO 26
<211> LENGTH: 42
<212> TYPE: PRT
<213> ORGANISM: artificial sequence
<220> FEATURE:
<223> OTHER INFORMATION: peptide construct
<220> FEATURE:
<221> NAME/KEY: MISC_FEATURE
<222> LOCATION: (1)..(1)
<223> OTHER INFORMATION: represents SEQ ID NO 12 i.e. amino acids from
      95-118 of beta-pleated sheet of MHC Class I
```

-continued

<400> SEQUENCE: 26

```
Gly Gly Gly Gly Ser Asn Gly Gln Glu Glu Lys Ala Gly Val Val Ser
1               5                   10                  15

Thr Gly Leu Ile Gly Gly Gly Lys Tyr Val Gly Ala Lys Glu Glu Ala
            20                  25                  30

Thr Phe Ser Leu Val Asp Phe Ala Ser Asp
        35                  40
```

<210> SEQ ID NO 27
<211> LENGTH: 37
<212> TYPE: PRT
<213> ORGANISM: artificial sequence
<220> FEATURE:
<223> OTHER INFORMATION: peptide construct
<220> FEATURE:
<221> NAME/KEY: PEPTIDE
<222> LOCATION: (6)..(6)
<223> OTHER INFORMATION: represents SEQ ID NO 13 i.e. amino acids 99-113 of beta-pleated sheet of MHC Class I

<400> SEQUENCE: 27

```
Asn Gly Gln Glu Glu Asp Ala Gly Val Val Ser Thr Gly Leu Ile Gly
1               5                   10                  15

Gly Gly Asp Ser Ala Phe Asp Val Leu Ser Phe Thr Ala Glu Glu Lys
            20                  25                  30

Ala Gly Val Tyr Lys
        35
```

<210> SEQ ID NO 28
<211> LENGTH: 37
<212> TYPE: PRT
<213> ORGANISM: artificial sequence
<220> FEATURE:
<223> OTHER INFORMATION: peptide construct
<220> FEATURE:
<221> NAME/KEY: PEPTIDE
<222> LOCATION: (5)..(5)
<223> OTHER INFORMATION: represents SEQ ID NO 15 i.e. amino acids 100-118 of beta-pleated sheet of MHC Class I
<220> FEATURE:
<221> NAME/KEY: PEPTIDE
<222> LOCATION: (7)..(7)
<223> OTHER INFORMATION: represents SEQ ID NO 13 i.e. amino acids 99-113 of beta-pleated sheet of MHC Class I

<400> SEQUENCE: 28

```
Asn Gly Gln Glu Glu Asp Ala Gly Val Val Ser Thr Gly Leu Ile Gly
1               5                   10                  15

Gly Gly Asp Ser Ala Phe Asp Val Leu Ser Phe Thr Ala Glu Glu Lys
            20                  25                  30

Ala Gly Val Tyr Lys
        35
```

<210> SEQ ID NO 29
<211> LENGTH: 37
<212> TYPE: PRT
<213> ORGANISM: artificial sequence
<220> FEATURE:
<223> OTHER INFORMATION: peptide construct
<220> FEATURE:
<221> NAME/KEY: MISC_FEATURE
<222> LOCATION: (6)..(6)
<223> OTHER INFORMATION: Xaa is a single amino acid other than Lys or is not present
<220> FEATURE:
<221> NAME/KEY: MISC_FEATURE -continued

```
<222> LOCATION: (6)..(9)
<223> OTHER INFORMATION: if any x is not present it is understood that
      subsequent positions will be shifted without any change to recited
      features
<220> FEATURE:
<221> NAME/KEY: MISC_FEATURE
<222> LOCATION: (7)..(7)
<223> OTHER INFORMATION: Xaa is a single amino acid other than Lys or is
      not present
<220> FEATURE:
<221> NAME/KEY: MISC_FEATURE
<222> LOCATION: (8)..(8)
<223> OTHER INFORMATION: Xaa is a single amino acid other than Lys or is
      not present
<220> FEATURE:
<221> NAME/KEY: MISC_FEATURE
<222> LOCATION: (9)..(9)
<223> OTHER INFORMATION: Xaa is a single amino acid other than Lys or is
      not present
<220> FEATURE:
<221> NAME/KEY: MISC_FEATURE
<222> LOCATION: (18)..(19)
<223> OTHER INFORMATION: A direct bond or a divalent spacer or linker

<400> SEQUENCE: 29

Asn Gly Gln Glu Glu Xaa Xaa Xaa Xaa Ala Gly Val Val Ser Thr Gly
1               5                   10                  15

Leu Ile Asp Ser Ala Phe Asp Val Leu Ser Phe Thr Ala Glu Glu Lys
            20                  25                  30

Ala Gly Val Tyr Lys
        35


<210> SEQ ID NO 30
<211> LENGTH: 37
<212> TYPE: PRT
<213> ORGANISM: artificial sequence
<220> FEATURE:
<223> OTHER INFORMATION: peptide construct
<220> FEATURE:
<221> NAME/KEY: MISC_FEATURE
<222> LOCATION: (20)..(20)
<223> OTHER INFORMATION: A direct bond or a divalent spacer or linker
<220> FEATURE:
<221> NAME/KEY: MISC_FEATURE
<222> LOCATION: (25)..(28)
<223> OTHER INFORMATION: if any x is not present it is understood that
      subsequent positions will be shifted without any change to recited
      features
<220> FEATURE:
<221> NAME/KEY: MISC_FEATURE
<222> LOCATION: (27)..(27)
<223> OTHER INFORMATION: Xaa is a single amino acid other than Lys or is
      not present
<220> FEATURE:
<221> NAME/KEY: MISC_FEATURE
<222> LOCATION: (25)..(25)
<223> OTHER INFORMATION: Xaa is a single amino acid other than Lys or is
      not present
<220> FEATURE:
<221> NAME/KEY: MISC_FEATURE
<222> LOCATION: (26)..(26)
<223> OTHER INFORMATION: Xaa is a single amino acid other than Lys or is
      not present
<220> FEATURE:
<221> NAME/KEY: MISC_FEATURE
<222> LOCATION: (28)..(28)
<223> OTHER INFORMATION: Xaa is a single amino acid other than Lys or is
      not present

<400> SEQUENCE: 30

Asp Ser Ala Phe Asp Val Leu Ser Phe Thr Ala Glu Glu Lys Ala Gly
1               5                   10                  15

Val Tyr Lys Asn Gly Gln Glu Glu Xaa Xaa Xaa Xaa Ala Gly Val Val
```

-continued

```
            20                  25                  30

Ser Thr Gly Leu Ile
        35


<210> SEQ ID NO 31
<211> LENGTH: 36
<212> TYPE: PRT
<213> ORGANISM: artificial sequence
<220> FEATURE:
<223> OTHER INFORMATION: peptide construct
<220> FEATURE:
<221> NAME/KEY: MISC_FEATURE
<222> LOCATION: (17)..(18)
<223> OTHER INFORMATION: A direct bond or one or more amino acids
<220> FEATURE:
<221> NAME/KEY: MISC_FEATURE
<222> LOCATION: (9)..(12)
<223> OTHER INFORMATION: if any x is not present it is understood that
      subsequent positions will be shifted without any change to recited
      features
<220> FEATURE:
<221> NAME/KEY: MISC_FEATURE
<222> LOCATION: (9)..(9)
<223> OTHER INFORMATION: Xaa is a single amino acid other than Ile or is
      not present
<220> FEATURE:
<221> NAME/KEY: MISC_FEATURE
<222> LOCATION: (10)..(10)
<223> OTHER INFORMATION: Xaa is a single amino acid other than Ile or is
      not present
<220> FEATURE:
<221> NAME/KEY: MISC_FEATURE
<222> LOCATION: (11)..(11)
<223> OTHER INFORMATION: Xaa is a single amino acid other than Ile or is
      not present
<220> FEATURE:
<221> NAME/KEY: MISC_FEATURE
<222> LOCATION: (12)..(12)
<223> OTHER INFORMATION: Xaa is a single amino acid other than Ile or is
      not present

<400> SEQUENCE: 31

Asp Leu Leu Lys Asn Gly Glu Arg Xaa Xaa Xaa Xaa Glu Lys Val Glu
1               5                   10                  15

Xaa Asp Ser Ala Phe Asp Val Leu Ser Phe Thr Ala Glu Glu Lys Ala
            20                  25                  30

Gly Val Tyr Lys
        35


<210> SEQ ID NO 32
<211> LENGTH: 35
<212> TYPE: PRT
<213> ORGANISM: artificial sequence
<220> FEATURE:
<223> OTHER INFORMATION: peptide construct
<220> FEATURE:
<221> NAME/KEY: MISC_FEATURE
<222> LOCATION: (20)..(20)
<223> OTHER INFORMATION: A direct bond or a divalent spacer or linker
<220> FEATURE:
<221> NAME/KEY: MISC_FEATURE
<222> LOCATION: (28)..(31)
<223> OTHER INFORMATION: if any x is not present it is understood that
      subsequent positions will be shifted without any change to recited
      features
<220> FEATURE:
<221> NAME/KEY: MISC_FEATURE
<222> LOCATION: (30)..(30)
<223> OTHER INFORMATION: Xaa is a single amino acid other than Ile or is
      not present
<220> FEATURE:
<221> NAME/KEY: MISC_FEATURE
<222> LOCATION: (31)..(31)
```

-continued

<223> OTHER INFORMATION: Xaa is a single amino acid other than Ile or is not present
<220> FEATURE:
<221> NAME/KEY: MISC_FEATURE
<222> LOCATION: (28)..(28)
<223> OTHER INFORMATION: Xaa is a single amino acid other than Ile or is not present
<220> FEATURE:
<221> NAME/KEY: MISC_FEATURE
<222> LOCATION: (29)..(29)
<223> OTHER INFORMATION: Xaa is a single amino acid other than Ile or is not present

<400> SEQUENCE: 32

```
Asp Ser Ala Phe Asp Val Leu Ser Phe Thr Ala Glu Glu Lys Ala Gly
1               5                   10                  15

Val Tyr Lys Asp Leu Leu Lys Asn Gly Glu Arg Xaa Xaa Xaa Xaa Glu
            20                  25                  30

Lys Val Glu
        35
```

<210> SEQ ID NO 33
<211> LENGTH: 37
<212> TYPE: PRT
<213> ORGANISM: artificial sequence
<220> FEATURE:
<223> OTHER INFORMATION: peptide construct
<220> FEATURE:
<221> NAME/KEY: MISC_FEATURE
<222> LOCATION: (10)..(10)
<223> OTHER INFORMATION: Xaa is a single amino acid other than Lys or is not present
<220> FEATURE:
<221> NAME/KEY: MISC_FEATURE
<222> LOCATION: (10)..(13)
<223> OTHER INFORMATION: if any x is not present it is understood that subsequent positions will be shifted without any change to recited features
<220> FEATURE:
<221> NAME/KEY: MISC_FEATURE
<222> LOCATION: (11)..(11)
<223> OTHER INFORMATION: Xaa is a single amino acid other than Lys or is not present
<220> FEATURE:
<221> NAME/KEY: MISC_FEATURE
<222> LOCATION: (12)..(12)
<223> OTHER INFORMATION: Xaa is a single amino acid other than Lys or is not present
<220> FEATURE:
<221> NAME/KEY: MISC_FEATURE
<222> LOCATION: (13)..(13)
<223> OTHER INFORMATION: Xaa is a single amino acid other than Lys or is not present
<220> FEATURE:
<221> NAME/KEY: MISC_FEATURE
<222> LOCATION: (18)..(19)
<223> OTHER INFORMATION: A direct bond or a divalent spacer or linker

<400> SEQUENCE: 33

```
Ile Leu Gly Thr Ser Val Val Gly Ala Xaa Xaa Xaa Xaa Glu Glu Gln
1               5                   10                  15

Gly Asn Asp Ser Ala Phe Asp Val Leu Ser Phe Thr Ala Glu Glu Lys
            20                  25                  30

Ala Gly Val Tyr Lys
        35
```

<210> SEQ ID NO 34
<211> LENGTH: 37
<212> TYPE: PRT
<213> ORGANISM: artificial sequence
<220> FEATURE:

-continued

```
<223> OTHER INFORMATION: peptide construct
<220> FEATURE:
<221> NAME/KEY: MISC_FEATURE
<222> LOCATION: (6)..(6)
<223> OTHER INFORMATION: Xaa is a single amino acid other than Lys or is
      not present
<220> FEATURE:
<221> NAME/KEY: MISC_FEATURE
<222> LOCATION: (6)..(9)
<223> OTHER INFORMATION: if any x is not present it is understood that
      subsequent positions will be shifted without any change to recited
      features
<220> FEATURE:
<221> NAME/KEY: MISC_FEATURE
<222> LOCATION: (7)..(7)
<223> OTHER INFORMATION: Xaa is a single amino acid other than Lys or is
      not present
<220> FEATURE:
<221> NAME/KEY: MISC_FEATURE
<222> LOCATION: (9)..(9)
<223> OTHER INFORMATION: Xaa is a single amino acid other than Lys or is
      not present
<220> FEATURE:
<221> NAME/KEY: MISC_FEATURE
<222> LOCATION: (8)..(8)
<223> OTHER INFORMATION: Xaa is a single amino acid other than Lys or is
      not present
<220> FEATURE:
<221> NAME/KEY: MISC_FEATURE
<222> LOCATION: (18)..(19)
<223> OTHER INFORMATION: A direct bond or a divalent spacer or linker

<400> SEQUENCE: 34

Asn Gly Gln Glu Glu Xaa Xaa Xaa Xaa Ala Gly Val Val Ser Thr Gly
1               5                   10                  15

Leu Ile Lys Tyr Val Gly Ala Lys Glu Glu Ala Thr Phe Ser Leu Val
            20                  25                  30

Asp Phe Ala Ser Asp
        35


<210> SEQ ID NO 35
<211> LENGTH: 37
<212> TYPE: PRT
<213> ORGANISM: artificial sequence
<220> FEATURE:
<223> OTHER INFORMATION: peptide construct
<220> FEATURE:
<221> NAME/KEY: MISC_FEATURE
<222> LOCATION: (18)..(19)
<223> OTHER INFORMATION: A direct bond or a divalent spacer or linker
<220> FEATURE:
<221> NAME/KEY: MISC_FEATURE
<222> LOCATION: (10)..(13)
<223> OTHER INFORMATION: if any x is not present it is understood that
      subsequent positions will be shifted without any change to recited
      features
<220> FEATURE:
<221> NAME/KEY: MISC_FEATURE
<222> LOCATION: (11)..(11)
<223> OTHER INFORMATION: Xaa is a single amino acid other than Lys or is
      not present
<220> FEATURE:
<221> NAME/KEY: MISC_FEATURE
<222> LOCATION: (12)..(12)
<223> OTHER INFORMATION: Xaa is a single amino acid other than Lys or is
      not present
<220> FEATURE:
<221> NAME/KEY: MISC_FEATURE
<222> LOCATION: (10)..(10)
<223> OTHER INFORMATION: Xaa is a single amino acid other than Lys or is
      not present
<220> FEATURE:
<221> NAME/KEY: MISC_FEATURE
<222> LOCATION: (13)..(13)
<223> OTHER INFORMATION: Xaa is a single amino acid other than Lys or is
```

-continued

```
     not present

<400> SEQUENCE: 35

Ile Leu Gly Thr Ser Val Val Gly Ala Xaa Xaa Xaa Xaa Glu Glu Gln
1               5                   10                  15

Gly Asn Lys Tyr Val Gly Ala Lys Glu Glu Ala Thr Phe Ser Leu Val
            20                  25                  30

Asp Phe Ala Ser Asp
        35


<210> SEQ ID NO 36
<211> LENGTH: 16
<212> TYPE: PRT
<213> ORGANISM: artificial sequence
<220> FEATURE:
<223> OTHER INFORMATION: peptide construct

<400> SEQUENCE: 36

Gly Cys Asp Val Gly Pro Asp Gly Arg Leu Leu Arg Gly His Asp Gln
1               5                   10                  15
```